United States Patent
Lami et al.

(10) Patent No.: US 11,998,254 B2
(45) Date of Patent: Jun. 4, 2024

(54) ACCESSORY FOR BONE SURGERY, ADVANTAGEOUSLY FOR OPERATIVE ARTHROSCOPY

(71) Applicant: NEWCLIP INTERNATIONAL, Luxembourg (LU)

(72) Inventors: Damien Lami, Saint Cyr sur Mer (FR); Jean-Charles Grillo, Sanary sur Mer (FR); Jean-Pierre Podgorski, Sevremoine (FR); Grégoire Larche, Cholet (FR)

(73) Assignee: NEWCLIP INTERNATIONAL, Luxembourg (LU)

(*) Notice: Subject to any disclaimer, the term of this patent is extended or adjusted under 35 U.S.C. 154(b) by 841 days.

(21) Appl. No.: 16/770,349

(22) PCT Filed: Dec. 3, 2018

(86) PCT No.: PCT/EP2018/083386
§ 371 (c)(1),
(2) Date: Jun. 5, 2020

(87) PCT Pub. No.: WO2019/110531
PCT Pub. Date: Jun. 13, 2019

(65) Prior Publication Data
US 2021/0169537 A1    Jun. 10, 2021

(30) Foreign Application Priority Data

Dec. 5, 2017 (FR) .................................. 1761676

(51) Int. Cl.
*A61B 17/86*   (2006.01)
*A61B 17/90*   (2006.01)
*A61B 90/00*   (2016.01)

(52) U.S. Cl.
CPC .............. *A61B 17/86* (2013.01); *A61B 17/90* (2021.08); *A61B 2090/061* (2016.02); *A61B 2090/062* (2016.02)

(58) Field of Classification Search
CPC .............. A61B 17/86; A61B 2090/061; A61B 2090/062; A61B 17/90
See application file for complete search history.

(56) References Cited

U.S. PATENT DOCUMENTS

2009/0270875 A1* 10/2009 Poncet ............... A61B 17/1778
606/102
2009/0318923 A1* 12/2009 Burkhart ............. A61F 2/30734
606/87

(Continued)

FOREIGN PATENT DOCUMENTS

FR    2996114 A1    4/2014

OTHER PUBLICATIONS

International Search Report, dated Feb. 20, 2019, from corresponding PCT application No. PCT/EP2018/083386.

*Primary Examiner* — Zade Coley
*Assistant Examiner* — Diana Jones
(74) *Attorney, Agent, or Firm* — NIXON & VANDERHYE

(57) ABSTRACT

Disclosed is an accessory for bone surgery, advantageously for operative arthroscopy, suitable for positioning and attaching a bone fragment on a target bone surface. This accessory includes a body of a sighting body including at least one sighting hole which opens on the two end faces, and a feeler member, extending in protrusion from the front end face of the sighting body. A front end face of the sighting body and a lower face of the feeler member together form a dihedral receiving surface against which the bone fragment is intended to bear. This accessory also includes pressing (Continued)

element capable of temporarily maintaining the bone fragment bearing against the dihedral receiving surface.

17 Claims, 3 Drawing Sheets

(56) References Cited

U.S. PATENT DOCUMENTS

| | | | | |
|---|---|---|---|---|
| 2015/0230808 A1* | 8/2015 | Boileau | ............... | A61B 17/1796 606/80 |
| 2016/0113757 A1* | 4/2016 | Diduch | ............... | A61B 17/8894 606/104 |
| 2017/0181759 A1* | 6/2017 | Bouduban | ........... | A61B 17/1778 |

* cited by examiner

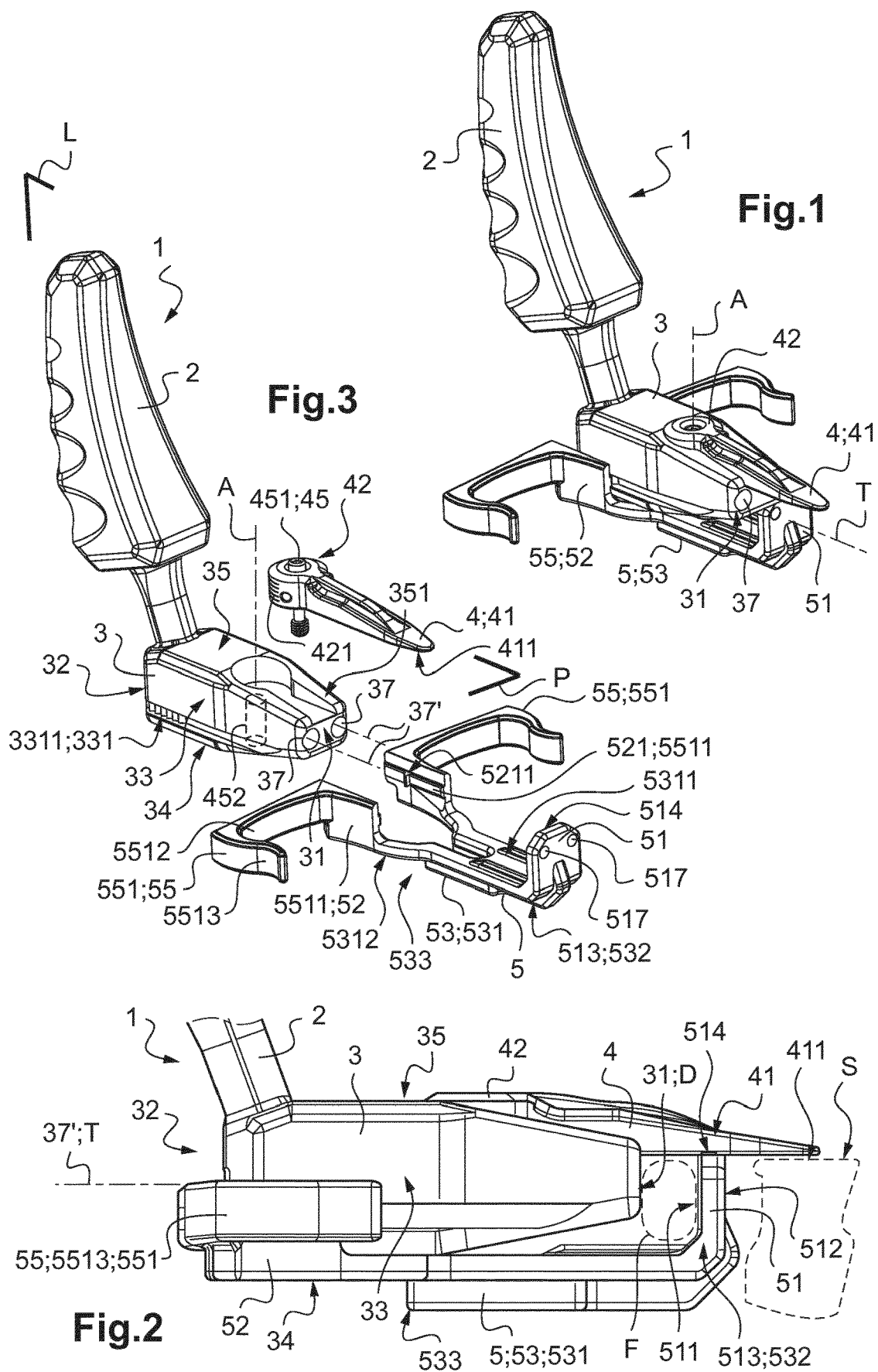

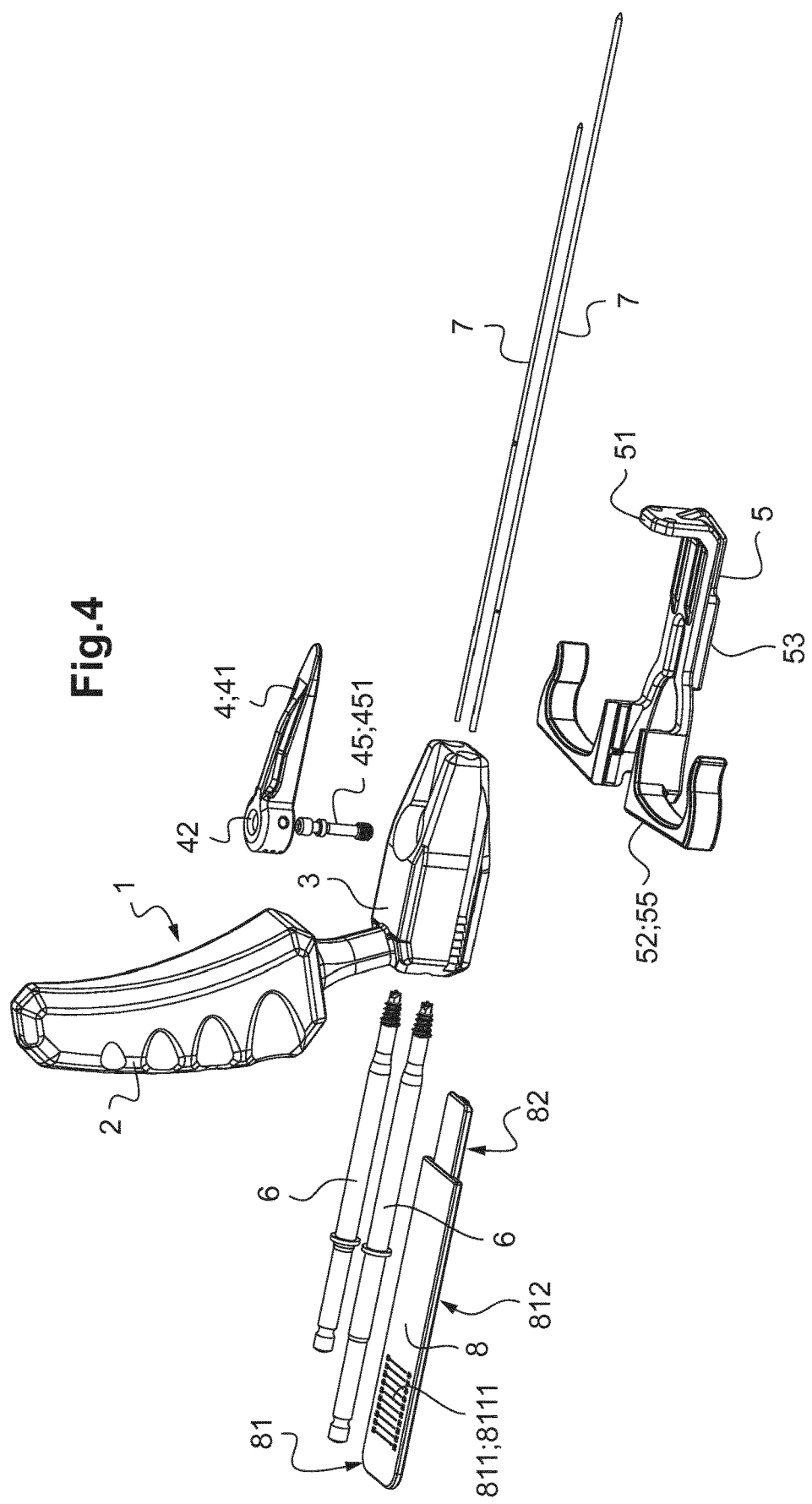

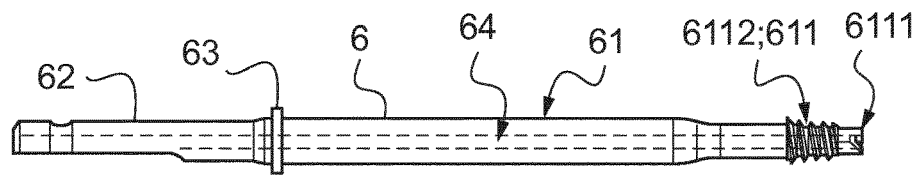
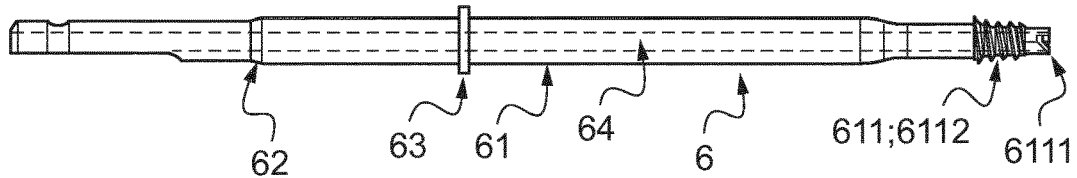
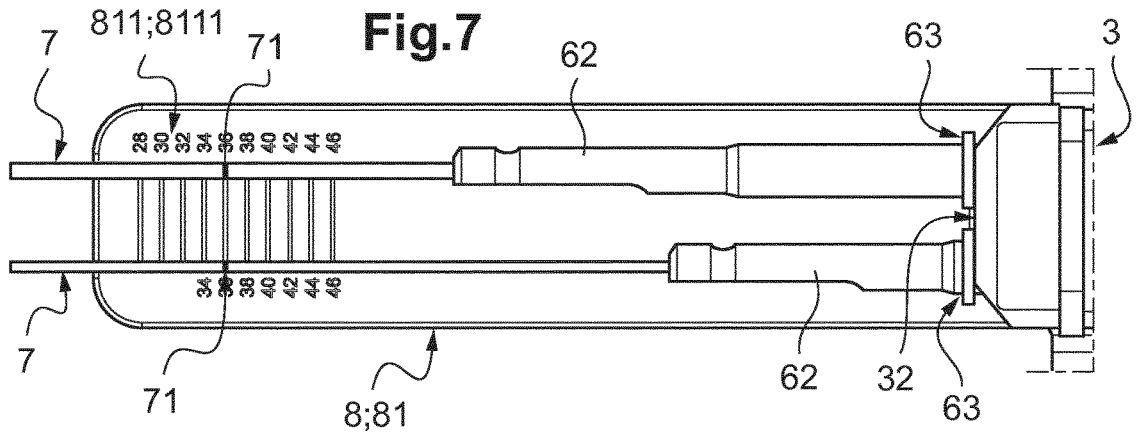
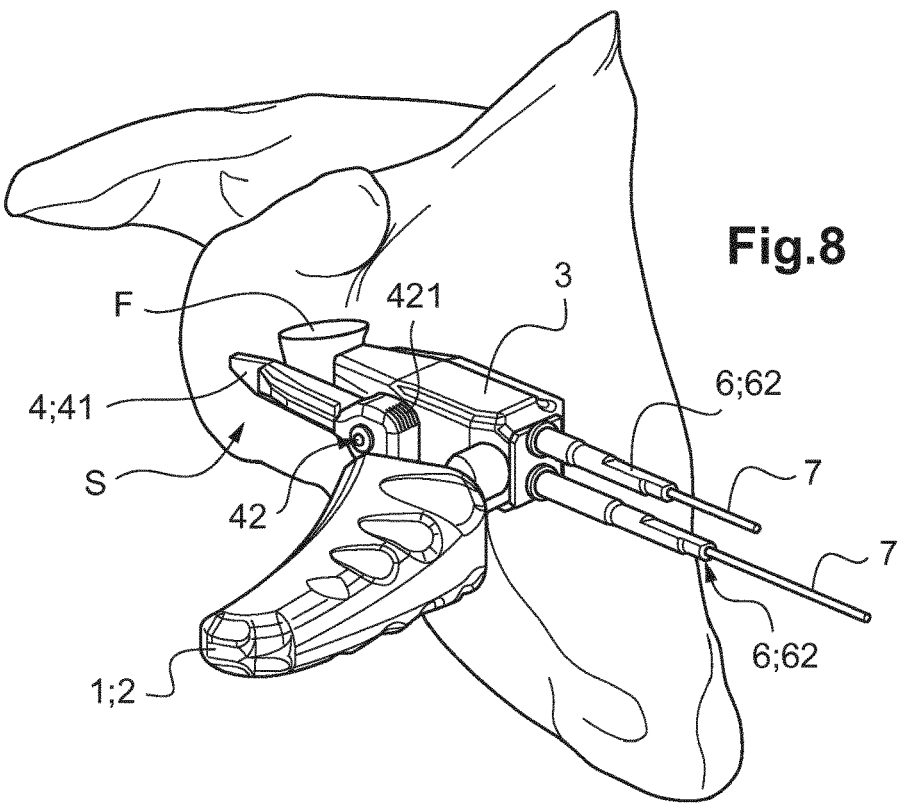

ACCESSORY FOR BONE SURGERY, ADVANTAGEOUSLY FOR OPERATIVE ARTHROSCOPY

TECHNICAL FIELD TO WHICH THE INVENTION RELATES

The present invention generally relates to the field of bone surgery.

It relates in particular to the ancillaries for bone surgery, advantageously for operative arthroscopy (for example, for a Latarjet procedure), operable for positioning and fixing a bone fragment on a target bone surface.

TECHNOLOGICAL BACK-GROUND

Certain bone surgery techniques recommend cutting a bone fragment, before positioning and fixing it on a target bone surface.

This is for example the case in the Latarjet procedure (or "coracoid bone block abutment") that consists in placing, in front of the shoulder, a bone block (coracoid) and a tendon (coraco-biceps) normally fixed thereto.

This operation is generally made on patients having dislocating shoulders, whose damaged anatomic structures are not repairable or are not sufficient to stabilize the shoulder.

The Latarjet "open-air" procedure is at present the standard technique.

An arthroscopic procedure has also been developed in order, in particular, to position the abutment more accurately and to perform, if need be, in the same operative time, an associated operation on the soft tissues.

However, despite the simplicity of its principle, the current ancillaries are sources of technical difficulties that may cause severe complications and that require long operation times.

Given the above, there exists a need for new ancillaries for bone surgery, advantageously for operative arthroscopy, which could combine a procedure that is fast and the less traumatic possible, while ensuring an accurate positioning of the bone fragment then a solid fixing on the target bone surface.

OBJECT OF THE INVENTION

In order to remedy the above-mentioned drawback of the state of the art, the present invention proposes an ancillary for bone surgery, advantageously for operative arthroscopy (for example, for a Latarjet procedure), operable for positioning and fixing a bone fragment on a target bone surface.

This ancillary comprises:
(i) at least one operating handle,
(ii) a sighting (or aiming or targeting) body comprising—
  two opposite end faces, a front one and a rear one, and—at least one sighting (or aiming or targeting) hole (for example, one or two) that opens to said two end faces, for guiding at least one screw and/or pin intended to be implanted into said bone fragment and into said target bone surface,
(iii) a feeler element, protruding from the front end face of said sighting body and having a lower face intended to bear against a part of said target bone surface.

The front end face of said sighting body and the lower face of said feeler element form together a dihedral receiving surface against which said bone fragment is intended to bear.

According to the invention, said ancillary comprises pressing means operable for temporarily holding said bone fragment bearing against said dihedral receiving surface.

The ancillary for bone surgery according to the invention thus facilitates the operative process, in particular within the framework of a Latarjet procedure.

This ancillary has in particular for advantage to allow a correct, fast and reproducible positioning of the bone fragment on its target bone surface.

According to a preferred embodiment, the pressing means comprise:
  a bearing panel arranged opposite the front end face of said sighting body, and
  translational guiding means, operable for guiding said bearing panel in translation along a translation axis directed parallel to said at least one sighting hole of the sighting body so as to ensure its spacing adjustment with respect to said front end face of the sighting body.

Other non-limitative and advantageous characteristics of this preferred embodiment, taken individually or according to all the technically possible combinations, are the following:
  the bearing panel of the pressing means comprises at least one recess formed opposite said at least one sighting hole equipping the sighting body;
  the pressing means cooperate with said sighting body through said translational guiding means; the pressing means and said sighting body cooperate through at least one rib/groove couple; the sighting body preferably comprises two lateral faces each comprising a first element of said rib/groove couple, and the pressing means comprise a base that carries the bearing panel and that is provided with a second element of said rib/groove couple; still preferably, the base of the pressing means comprise a lower panel, opposite a lower face of said sighting body, wherein said lower panel comprises two ends: a first end provided with the bearing panel, and a second end provided with translational guiding means;
  the pressing means comprise gripping means, advantageously carried by said base, for the translational operation of said bearing panel by an operator; the gripping means of said pressing means advantageously comprise two lateral hooks that extend on either side of the sighting body and that open opposite said bearing panel;
  the translational guiding means comprise indexing means (for example, a set of teeth), for providing said bearing panel with a translational pitch, for example a pitch comprised between 1 and 3 mm; the pressing means advantageously comprise mean for deactivating said indexing means, in particular for operating said bearing panel so as to space it from to the front end face of said sighting body.

Other non-limitative and advantageous characteristics of the ancillary according to the invention, taken individually or according to all the technically possible combinations, are the following:
  the pressing means are removable with respect to said ancillary;
  the feeler element cooperates with said sighting body through height adjustment means, along a second translation axis directed perpendicular to the axis of said at least one sighting hole; the feeler element advantageously carries a metric scaling directed along said second translation axis;

the sighting body comprises two through-holes juxtaposed and coplanar to each other in a sighting plane; said at least one handle advantageously extends in a plane perpendicular, or at least approximately perpendicular, to said sighting plane.

The invention also proposes a system of ancillaries, capable of being coupled to an arthroscopy, comprising:
(i) at least one first ancillary according to the invention,
(ii) at least one second ancillary of the screw type;
wherein said at least one second ancillary comprises:
an upstream portion, intended to enter said sighting hole of the sighting body and to protrude from said front end face, which comprises an upstream end forming a drilling/screwing head and a progressive thread profile, and
a downstream portion, intended to cooperate with a rotational operation member,
an abutment structure arranged between said upstream and downstream portions, adapted to come into abutment against the rear end face of the sighting body, and
a central channel, arranged coaxially to said second ancillary, adapted to the passage of a pin.

Preferably, the system of ancillaries comprises two second ancillaries having downstream portions of different lengths with respect to each other.

The system of ancillaries also advantageously comprises a ruler having:
a first measurement portion provided with a scaling, for measuring the depth of penetration of a pin into the bone fragment and the target bone surface,
a second measurement portion provided with a scaling, for measuring the width of the bone fragment, and
a portion for the assembly to the sighting body, at its rear end face.

The invention also proposes a bone surgery method, advantageously hybrid "open-air/arthroscopy", comprising:
measuring the width of the bone fragment, advantageously by means of said ruler,
adjusting the height of the feeler element of the first ancillary taking into account the measurement obtained with the ruler,
holding the bone fragment against the dihedral bearing surface of the first ancillary, thanks to the pressing means,
inserting at least one second ancillary through said at least one sighting hole equipping the sighting body and into said bone fragment,
removing the pressing means,
positioning the bone fragment against the target bone surface,
inserting at least one pin through said at least second ancillary,
measuring the depth of insertion of said at least one pin, by means of the ruler, to determine the length of said at least one compression screw to be installed,
removing successively each second ancillary and replacing it by said compression screw.

DETAILED DESCRIPTION OF AN EXEMPLARY EMBODIMENT

The following description in relation with the appended drawings, given by way of non-limitative example, will allow a good understanding of what the invention consists of and of how it can be implemented.

In the appended drawings:
FIG. 1 in an overall and perspective view of an ancillary for bone surgery, advantageously for operative arthroscopy (for example, for a Latarjet procedure),
FIG. 2 is a partial and enlarged side view of the ancillary according to FIG. 1;
FIG. 3 in an overall and perspective exploded view of the ancillary according to FIGS. 1 and 2;
FIG. 4 shows a system of ancillaries according to the invention, comprising in particular the ancillary according to FIGS. 1 to 3;
FIGS. 5 and 6 show ancillaries of the gripper/screwdriver type, part of the system of ancillaries according to FIG. 4;
FIG. 7 is a top view of a ruler belonging to the system of ancillaries according to FIG. 4;
FIG. 8 shows the implementation of the system of ancillaries according to the invention, during a Latarjet bone surgery procedure.

ANCILLARY FOR BONE SURGERY

FIGS. 1 to 3 show an ancillary 1 according to the invention that is operable for bone surgery, advantageously for operative arthroscopy.

Operative arthroscopy allows mini-invasive, intra-articular surgical procedures.

In particular, the ancillary 1 according to the invention is operable for positioning and fixing a bone fragment F on a target bone surface S (FIG. 8).

Such an ancillary 1 is particularly suitable for performing a Latarjet procedure.

This Latarjet procedure is a surgical operation during which the bone fragment F is used as a bone abutment intended to be positioned at the anterior part of the glenoid cavity; this bone abutment is made from the coracoid apophysis.

The ancillary 1 according to the invention, also called "sighting (or aiming or targeting) ancillary" or "sighting (or aiming or targeting) guide", comprises for that purpose different parts:
an operating handle 2,
a sighting (or aiming or targeting) body 3, operable for guiding at least one screw and/or pin intended to be implanted into the bone fragment F (for example, the coracoid apophysis) and/or into the target bone surface S (for example, the anterior part of the glenoid cavity),
a feeler element 4, intended to bear against a part of the target bone surface S, and
pressing means 5 comprising in particular a bearing panel 51, operable for temporarily holding the bone fragment F within the ancillary 1.

The sighting body 3 is here in the form of a generally parallelepipedal block.

This sighting body 3 is delimited by a set of faces (FIGS. 2 and 3):
two opposite end faces, a front one 31 and a rear one 32,
two opposite lateral faces 33,
a so-called "lower" face 34, and
a so-called "upper" face 35.

This sighting body 3 comprises at least one sighting (or aiming or targeting) hole 37, here two in number (FIG. 3). Each sighting hole 37 is operable for guiding at least one screw and/or one pin intended to be implanted into the bone fragment F and/or into the target bone surface S.

Each sighting hole 37 is here a through-hole: it opens to the two above-mentioned end faces 31, 32.

The sighting holes 37 each define a longitudinal axis 37'. The longitudinal axes 37' here extend parallel to each other, juxtaposed and coplanar to each other in a general plane P that is also called "sighting (or aiming or targeting) plane" (FIG. 3).

The two lateral faces 33 here comprise translational guiding means 331 that are intended to cooperate with the pressing means 5 for guiding these latter in translation.

These translational guiding means 331 here comprise a first element 331 of a rib/groove couple, here a groove extending parallel to the longitudinal axis 37' of the sighting holes 37 (FIG. 3).

This groove 331 here comprises indexing means, for example a set of teeth 3311 (several teeth distributed over the length of the groove 331), for providing the bearing panel 51 with a translational pitch. This translational pitch is for example comprised between 1 and 3 mm.

As described hereinafter, such a translational pitch is interesting to ensure a removable holding of the spacing adjustment applied to the bearing panel 51 during the pinching of the bone fragment F.

The feeler element 4 comprises two portions:
a front portion 41, protruding from the front end face 31 of the sighting body 3, and
a rear portion 42, arranged at the upper face 35 of the sighting body 3 for its detachable fixing to the latter.

The rear portion 42 of the feeler element 4 is herein placed within a housing 351 (or imprint) that is formed in the upper face 35 of the sighting body 3 (FIG. 3).

This rear portion 42 of the feeler element 4 cooperates with the sighting body 3 through height adjustment means 45, along a translation axis A directed perpendicular to the longitudinal axis 37' of the sighting holes 37.

The rear part 42 of the feeler element 4 is guided in translation by the complementary housing 351.

For that purpose, the rear portion 42 of the feeler element 4 carries a screw 451 (with a rotational degree of freedom and no translational degree of freedom) that cooperates with a threaded hole 452 (schematically shown in FIG. 3), directed coaxially with respect to said translation axis A.

The height stroke of this feeler element 4 goes for example from 0 mm to 6 mm, corresponding to an offset from 3.5 to 9.5 mm.

The rear portion 42 of the feeler element 4 also carries a metric scaling 421 that is directed along the above-mentioned translation axis A.

This metric scaling 421 is intended to serve as a landmark for the height adjustment of the feeler element 4, taking into account the dimensions of the bone fragment F.

This metric scaling 421 is formed on the rear portion 42, laterally and over the height thereof, so as to use the upper face 35 of the sighting body 3 as a height adjustment landmark.

For its part, the front portion 41 of this feeler element 4 has a lower face 411 that is intended, as described hereinafter, to bear simultaneously against the bone fragment F and a part of the target bone surface S.

This lower face 411 of the feeler element 4 forms, in combination with the front end face 31 of the sighting body 3, a dihedral receiving surface D against which the bone fragment F is intended to bear and to be held by the pressing means 5 (FIG. 2).

The pressing means 5 are operable for temporarily holding the bone fragment F bearing against this dihedral receiving surface D (FIG. 2). These pressing means 5 are moreover advantageously removable with respect to the ancillary 1, useful during the positioning and fixing of the bone fragment F.

The pressing means 5 here comprise:
the bearing panel 51 arranged opposite the front end face 31 of the sighting body 3,
the translational guiding means 52, operable for guiding this bearing panel 51 in translation along a translation axis T (FIG. 2), directed parallel to the longitudinal axis 37' of the sighting holes 37 of the sighting body 3, and
a base 53 carrying this bearing panel 51 and these translational guiding means 52.

The base 53 here comprises a lower panel 531, intended to come opposite the lower face 34 of the sighting body 3.

This lower panel 531 comprises two ends:
a first, front end 532, provided with the bearing panel 51, and
a second, rear end 533, provided with the translational guiding means 52.

This lower panel 531 has here a generally Y or fork shape (FIG. 3), comprising:
a front arm 5311 carrying the bearing panel 51, and
two rear legs 5312 carrying the translational guiding means 52.

This embodiment of the base 53 aims to allow an elastic deformation spacing the rear legs 5312 with respect to the associated translational guiding means 52.

The bearing panel 51 comprises different portions (FIGS. 2 and 3):
a rear face 511, directed towards the front end face 31 of the sighting body 3,
a front face 512, opposed to said rear face 511,
a lower edge 513, integral with the base 53, and
an upper, free edge 514, intended to come opposite and to travel along the lower face 411 of the feeler element 4.

The bearing panel 51, and in particular the rear face 511 thereof, comprises at least one recess 517 (blind or through) arranged opposite each sighting hole 37 equipping the sighting body 3.

Each recess 517 is useful to receive the free end of an ancillary brought through the coaxial sighting hole 37 (in particular, a second ancillary 6 described hereinafter in relation with FIG. 4).

The translational guiding means 52 allow the spacing adjustment of the bearing panel 51 with respect to the front end face 31 of the sighting body 3; in other words, the translational guiding means 52 allow guiding the bearing panel 51 in translation, parallel to each other, along the translation axis T.

These translational guiding means 52 here further allow a separation of the pressing means 5 with respect to the sighting body 3, by an extraction move on the side of the front end face 31 of the sighting body 3.

For that purpose, the translational guiding means 52 of the pressing means 5 here cooperate with the translational guiding means 311 of the sighting body 3.

These translational guiding means 52 here comprise a second element 521 of the rib/groove couple adapted to cooperate, to within a clearance, with the first element 311 of the rib/groove couple of the sighting body 3 (FIG. 3).

The second element 521 of the rib/groove couple, here a rib, comprises indexing means, for example at least one tooth 5211, intended to cooperate by elastic deformation with the indexing means 3311 of the groove 311 equipping the sighting body 3.

The pressing means 5 also comprise gripping means 55, here carried by the rear end 533 of the base 53 and by the translational guiding means 52.

The gripping means 55 are operable for the translational operation by an operator of the pressing means 5 and the bearing panel 51 thereof, in particular in a direction moving the bearing panel 51 closer to the front end face 31 of the sighting body 3.

The gripping means 55 comprise for that purpose two lateral hooks 551, having here a generally U shape, which extend on either side of the sighting body 3 (here symmetrically) and which open opposite the bearing panel 51.

Here, each lateral hook 551 comprises:
- an inner section 5511, intended to bear on one of the lateral faces 33 of the sighting body 3 and provided with the second element 521 of the rib/groove couple,
- a transverse section 5512, serving as a traction bearing surface for the operator, and
- an outer section 5513, opposite and remote from the inner section 5511.

The two inner sections 5511 of the lateral hooks 551 hence extend opposite and remote from each other. They are intended to take in sandwich the lateral faces 33 of the sighting body 3.

The pressing means 5 here also comprise, optionally, means for deactivating the indexing means 3311, 5211, in particular for a free operation spacing the bearing panel 51 from the front end face 31 of the sighting body 3 during the disassembly of the pressing means 5.

These means for deactivating the indexing means 3311, 5211 are here formed by the outer section 5513 of the lateral hooks 551.

Indeed, a pinching force aiming to move the two outer sections 5513 closer to each other tends to space apart and make diverge the inner sections 5511 of the lateral hooks 551 by a phenomenon of elastic deformation, then leading to the spacing of the indexing means 5211 of the ribs 521 with respect to the indexing means 3311 of the grooves 331. The pressing means 5 are then free to slide over the length of the sighting body 3, which is in particular useful to separate these pressing means 5 from the ancillary 1.

To be complete, the handle 2 is here made integral with the upper face 35 of the sighting body 3, on the side of the rear front face 32.

This handle 2 advantageously extends in a plane L perpendicular, or at least approximately perpendicular, to the sighting plane P.

In practice, this arrangement of the handle 2 is particularly ergonomic for the practitioner, during the operative process.

System of Ancillaries

The ancillary 1 according to the invention, described hereinabove in relation with FIGS. 1 to 3, advantageously belongs to a system of ancillaries, capable of being coupled to an arthroscopy, which is schematically shown in FIG. 4.

This system of ancillaries comprises:
- at least one first ancillary 1 described hereinabove in relation with FIGS. 1 to 3,
- a second ancillary 6 of the screw type, here having a gripper/screwdriver function,
- at least one pin 7,
- compression screws (not shown), preferably cannulated compression screws, and advantageously
- a ruler 8.

The second ancillaries 6 of the screw type, shown in detail in FIGS. 5 and 6, are in particular useful for temporarily holding the bone fragment F on the ancillary 1 after disassembly of the pressing means 5.

These second ancillaries 6 comprise:
- an upstream portion 61, intended to enter the sighting hole 37 of the sighting body 3 and to protrude from the front end face 31,
- a downstream portion 62, intended to cooperate with a rotational operation member (not shown) that has advantageously the shape of a screwdriver handle,
- an abutment structure 63 formed between the upstream 61 and downstream 62 portions, adapted to come into abutment against the rear end face 32 of the sighting body 3, and
- a central channel 64, arranged coaxially to the body of this second ancillary 6, adapted to the passage of the above-mentioned pin 7 (as schematically illustrated in FIG. 7).

The upstream portion 61 has a diameter corresponding, to within a clearance, to the diameter of the sighting hole 37 of the sighting body 3.

This upstream portion 61 has an upstream end 611 that is composed of two portions, in series:
- a terminal drilling/screwing head 6111, and
- progressive thread profile 6112.

The drilling/screwing head 6111 has a structure having two functions:
- a drilling head function for drilling into the bone fragment F placed against the dihedral receiving surface D, and
- a screwing head function for a head of a compression screw intended to be implanted between the bone fragment F and the target bone surface S.

The progressive thread profile 6112 is adapted to be screwed into the bone fragment F.

The second ancillaries 6 are advantageously two in number and have advantageously downstream portions 62 that have different lengths with respect to each other. This length difference aims to avoid a conflicting encumbering during the operative process.

The ruler 8, generally plate-shaped, advantageously comprises the following portions:
- a rear portion 81 adapted for the implementation of different measurements, and
- a front portion 82 adapted for the assembly to the sighting body 3, at its rear end face 32.

The rear portion 81 has two faces provided with measurement portions:
- an upper face 811 forming a first measurement portion provided with a metric scaling 8111, for measuring the depth of penetration of a pin 7 into the bone fragment F and the target bone surface S, and
- a lower face 812 forming a second measurement portion provided with a metric scaling (not shown), for measuring the width of the bone fragment F.

The front portion 82 forms a part of a tenon/mortise assembly.

This front portion 82 here have a tenon shape intended to be received into a complementary housing (not shown) opening on the side of the rear end face 32 of the sighting body 3.

The ruler 8 is hence adapted to be mounted on the sighting body 3, in protrusion from its rear end face 32, so as to extend opposite a section of pins 7 coming from the side of this rear end face 32.

The pins 7 are intended to allow the guided packing and the validation of the centring and of the centre distance of the future compression screws.

These pins 7 advantageously comprise a visual landmark 71 to determine their depth of penetration by means of the metric scaling 8111 of the first measurement portion 811 (FIG. 7).

The metric scaling 8111 of the first measurement portion 811 is adjusted as a function of the length of the pins 7 and of the position of its visual landmark 71.

In practice, the depth of penetration of each pin 7 is obtained by reading the value of the metric scaling 8111 that is located opposite the visual landmark 71 of this pin 7.

Method

The system of ancillaries according to the invention allows combining a procedure that is the less traumatic possible, while ensuring a fast and accurate positioning of the bone fragment then a solid fixing on the target bone surface.

In practice, the bone surgery method first comprises extracting and preparing, according to a conventional procedure, the bone fragment F, for example the coracoid bone block (with the coraco-biceps tendon) during a Latarjet procedure.

The bone surgery method then comprises the following steps in succession, for preparing the first ancillary 1 and for attaching the first ancillary 1 with the bone fragment F, i.e.:

- measuring the width of the bone fragment F, preferably in its three planes, advantageously by means of the ruler 8 (more precisely by means of the second measurement portion 812),
- adjusting the height of the feeler element 4 of the first ancillary 1 taking into account the measurement obtained with the ruler 8 in the axial plane,
- inserting a bone fragment F into the first ancillary 1 and operating the pressing means 5 so that its bearing panel 51 hold this bone fragment F by pinching with the dihedral bearing surface D of the first ancillary 1,
- inserting second ancillaries 6 through sighting orifices 37 equipping the sighting body 3, from the rear end face 32 thereof, so that the upstream end 611 of each second ancillary 6 opens on the side of the front end face 31 and is screwed into the bone fragment F, generating a temporary attachment first ancillary 1/bone fragment F (advantageously the shortest second ancillary 6 is firstly inserted to avoid the encumbering problems),
- removing the pressing means 5 with respect to the first ancillary 1, so that the bone fragment F is held against the dihedral bearing surface D of the first ancillary 1 through the second ancillaries 6 and so that the bone fragment F is released to be installed.

These different previous steps (extraction/preparation/fixing) are advantageously performed during an open-air time.

The bone surgery method then comprises the succession of the following steps for positioning and fixing the bone fragment F against the target bone surface S, advantageously during an arthroscopic time, i.e.:

- positioning the bone fragment F against the target bone surface S, guided in particular by the feeler element 4 that bears against a part of the target bone surface S, for example the articular surface of the glenoid cavity in a Latarjet procedure (FIG. 8),
- inserting the pins 7 within the second ancillaries 6 so that they each pass through the bone fragment F and the target bone surface S (FIG. 8),
- measuring the depth of insertion of the pins 7 by means of the ruler 8 (more precisely by means of the first measurement portion 811), to determine the length of the compression screws to be implanted (FIG. 7),
- removing successively each second ancillary 6 and replacing it by a compression screw that is guided through each sighting hole 37, over the length of a pin 7, and that is screwed by means of this second ancillary 6.

The bone fragment F is hence fixed to the target bone surface S through compression screws that pass through this bone fragment F and that are anchored to the target bone surface S.

Once the bone fragment F suitably fixed, the pins 7 and the first ancillary 1 can be removed.

The surgical method is hence advantageously hybrid "open-air/arthroscopy", comprising extracting and preparing the abutment in an open-air time then positioning and fixing the bone fragment F against the target bone surface S in an arthroscopic time.

The invention claimed is:

1. An ancillary for bone surgery, advantageously for operative arthroscopy, operable for positioning and fixing a bone fragment on a target bone surface,
wherein said ancillary (1) comprises:
(i) at least one operating handle (2),
(ii) a sighting body (3) comprising—two opposite end faces, a front one (31) and a rear one (32), and—at least one sighting hole (37) that opens to said two end faces (31, 32), for guiding at least one screw and/or pin intended to be implanted into said bone fragment (F) and into said target bone surface (S),
(iii) a feeler element (4), protruding from the front end face (31) of said sighting body (3) and having a lower face (411) intended to bear against a part of said target bone surface (S),
wherein said front end face (31) of said sighting body (3) and said lower face (411) of said feeler element (4) form together a dihedral receiving surface (D) against which said bone fragment (F) is intended to bear,
wherein said ancillary (1) comprises pressing means (5) operable for temporarily holding said bone fragment (F) bearing against said dihedral receiving surface (D),
wherein the pressing means (5) comprise:
a bearing panel (51) arranged opposite the front end face (31) of said sighting body (3), and
translational guiding means (52), for guiding said bearing panel (51) in translation along a translation axis (T) directed parallel to said at least one sighting hole (37) of the sighting body (3) so as to ensure its spacing adjustment with respect to said front end face (31) of the sighting body (3).

2. The ancillary for bone surgery according to claim 1, wherein the translational guiding means (52) of the pressing means (5) cooperate with translational guiding means (331) of said sighting body (3).

3. The ancillary for bone surgery according to claim 2, wherein the pressing means (5) comprise gripping means (55), advantageously carried by said base (53), for the translational operation of said bearing panel (51) by an operator.

4. The ancillary for bone surgery according to claim 2, wherein the pressing means (5) and the sighting body (3) cooperate through at least one rib/groove couple (331, 521).

5. The ancillary for bone surgery according to claim 4, wherein the sighting body (3) has two lateral faces (33) each comprising a first element (331) of said rib/groove couple, and wherein the pressing means (5) comprise a base (53) that carries the bearing panel (51) and that is provided with a second element (521) of said rib/groove couple.

6. The ancillary for bone surgery according to claim 5, wherein the base (53) of the pressing means (5) comprises a lower panel (531), opposite a lower face (34) of said sighting body (3),
wherein said lower panel (531) comprises two ends:
a first end (532) provided with the bearing panel (51), and
a second end (533) provided with translational guiding means (52).

7. The ancillary for bone surgery according to claim 4, wherein the pressing means (5) comprise gripping means (55), advantageously carried by said base (53), for the translational operation of said bearing panel (51) by an operator.

8. The ancillary for bone surgery according to claim 5, wherein the pressing means (5) comprise gripping means (55), advantageously carried by said base (53), for the translational operation of said bearing panel (51) by an operator.

9. The ancillary for bone surgery according to claim 1, wherein the pressing means (5) comprise gripping means (55), advantageously carried by said base (53), for the translational operation of said bearing panel (51) by an operator.

10. The ancillary for bone surgery according to claim 1, wherein the translational guiding means (331, 52) comprise indexing means (5211, 3311), for providing said bearing panel (51) with a translational pitch.

11. The ancillary for bone surgery according to claim 10, wherein the pressing means (5) comprise means (5513) for deactivating said indexing means (5211, 3311), in particular for operating said bearing panel (51) so as to space the bearing panel from the front end face (31) of said sighting body (3).

12. The ancillary for bone surgery according to claim 1, wherein the pressing means (5) are removable with respect to said ancillary (1).

13. The ancillary for bone surgery according to claim 1, wherein the sighting body (3) comprises two through-holes (37) juxtaposed and coplanar to each other in a sighting plane (P).

14. The ancillary for bone surgery according to claim 13, wherein said at least one handle (2) extends in a plane (L) perpendicular, or at least approximately perpendicular, to said sighting plane (P).

15. An ancillary for bone surgery, advantageously for operative arthroscopy, operable for positioning and fixing a bone fragment on a target bone surface,
wherein said ancillary (1) comprises:
(i) at least one operating handle (2),
(ii) a sighting body (3) comprising—two opposite end faces, a front one (31) and a rear one (32), and—at least one sighting hole (37) that opens to said two end faces (31, 32), for guiding at least one screw and/or pin intended to be implanted into said bone fragment (F) and into said target bone surface (S),
(iii) a feeler element (4), protruding from the front end face (31) of said sighting body (3) and having a lower face (411) intended to bear against a part of said target bone surface (S),
wherein said front end face (31) of said sighting body (3) and said lower face (411) of said feeler element (4) form together a dihedral receiving surface (D) against which said bone fragment (F) is intended to bear,
wherein said ancillary (1) comprises pressing means (5) operable for temporarily holding said bone fragment (F) bearing against said dihedral receiving surface (D),
wherein the feeler element (4) cooperates with said sighting body (3) through height adjustment means (45), along a second translation axis (A) directed perpendicular to the axis (37') of said at least one sighting hole (37).

16. A system of ancillaries, capable of being coupled to an arthroscopy, comprising:
(i) at least one first ancillary (1), advantageously for operative arthroscopy, operable for positioning and fixing a bone fragment on a target bone surface,
wherein said ancillary (1) comprises:
at least one operating handle (2),
a sighting body (3) comprising—two opposite end faces, a front one (31) and a rear one (32), and—at least one sighting hole (37) that opens to said two end faces (31, 32), for guiding at least one screw and/or pin intended to be implanted into said bone fragment (F) and into said target bone surface (S),
a feeler element (4), protruding from the front end face (31) of said sighting body (3) and having a lower face (411) intended to bear against a part of said target bone surface (S),
wherein said front end face (31) of said sighting body (3) and said lower face (411) of said feeler element (4) form together a dihedral receiving surface (D) against which said bone fragment (F) is intended to bear,
wherein said ancillary (1) comprises pressing means (5) operable for temporarily holding said bone fragment (F) bearing against said dihedral receiving surface (D),
(ii) at least one second ancillary (6) of the gripper/screwdriver type,
wherein said at least one second ancillary (6) comprises:
an upstream portion (61), intended to enter said sighting hole (37) of the sighting body (3) and to protrude at said front end face (31), which comprises an upstream end (611) forming a drilling/screwing head (6111) and a progressive thread profile (6112), and
a downstream portion (62), intended to cooperate with a rotational operation member,
an abutment structure (63) arranged between said upstream (61) and downstream (62) portions, adapted to come into abutment against the rear end face (32) of the sighting body (3), and
a central channel (64), arranged coaxially to said second ancillary (6), adapted to the passage of a pin (7).

17. The system of ancillaries according to claim 16, further comprising a ruler (8) having:
a first measurement portion (811) provided with a scaling (8111), for measuring the depth of penetration of a pin (7) into the bone fragment (F) and the target bone surface (S),
a second measurement portion (812) provided with a scaling, for measuring the width of the bone fragment (F), and
a portion (82) for the assembly to the sighting body (3), at its rear end face (32).

* * * * *